United States Patent
Conrado

(10) Patent No.: US 12,269,005 B2
(45) Date of Patent: Apr. 8, 2025

(54) PROCESS AND APPARATUS FOR PROVIDING A FEEDSTOCK

(71) Applicant: LanzaTech, Inc., Skokie, IL (US)

(72) Inventor: Robert John Conrado, Washington, DC (US)

(73) Assignee: LanzaTech, Inc., Skokie, IL (US)

( * ) Notice: Subject to any disclaimer, the term of this patent is extended or adjusted under 35 U.S.C. 154(b) by 98 days.

(21) Appl. No.: 17/658,594

(22) Filed: Apr. 8, 2022

(65) Prior Publication Data
US 2022/0323927 A1    Oct. 13, 2022

Related U.S. Application Data

(60) Provisional application No. 63/173,243, filed on Apr. 9, 2021.

(51) Int. Cl.
*B01J 19/24*         (2006.01)
*B01D 53/047*        (2006.01)
(Continued)

(52) U.S. Cl.
CPC ........ *B01J 19/2465* (2013.01); *B01D 53/047* (2013.01); *B01D 53/229* (2013.01);
(Continued)

(58) Field of Classification Search
CPC .................................................. B01J 19/2465
See application file for complete search history.

(56) References Cited

U.S. PATENT DOCUMENTS 4,545,976 A * 10/1985 Osman .................... C01B 3/382
                                                              252/373
8,119,099 B2    2/2012 Schiødt
(Continued)

FOREIGN PATENT DOCUMENTS

JP    2015077120 A    4/2015
WO    2007117157 A1   10/2007
(Continued)

OTHER PUBLICATIONS

Paula Kosonen, Techno-economic study of bioethanol production as a carbon capture and utilization process Master of Science Thesis Tampere University Master's Degree Program in Bioengineering Nov. 2020 (76 pages) p. 42.
(Continued)

*Primary Examiner* — Paul A Wartalowicz

(57) ABSTRACT

The disclosure is directed to a process and an apparatus for providing a feedstock. A gaseous feed stream comprising at least one hydrocarbon is passed to a reforming unit followed by a water gas shift reaction zone to provide a first gaseous stream comprising $H_2$, CO, and $CO_2$. The first gaseous stream is fed a hydrogen separation zone to separate it into a hydrogen enriched stream and a second gaseous stream comprising CO, $CO_2$ and $H_2$. The second gaseous stream is fed to a $CO_2$ to CO conversion system to produce a third gaseous stream comprising $H_2$ and CO having a $H_2$:CO molar ratio of less than 5:1. The third gaseous stream is fed as the feedstock for a gas fermentation unit to have increased stability and product selectivity.

13 Claims, 4 Drawing Sheets

(51) Int. Cl.
  *B01D 53/22* (2006.01)
  *C01B 3/48* (2006.01)
  *C12M 1/00* (2006.01)
  *C25B 1/23* (2021.01)
  *C25B 15/08* (2006.01)

(52) U.S. Cl.
  CPC .............. *C01B 3/48* (2013.01); *C12M 21/12* (2013.01); *C25B 1/23* (2021.01); *C25B 15/081* (2021.01); *B01D 2256/16* (2013.01); *B01D 2256/20* (2013.01); *B01D 2256/22* (2013.01); *B01D 2257/502* (2013.01); *B01D 2257/504* (2013.01); *C01B 2203/0205* (2013.01); *C01B 2203/0283* (2013.01); *C01B 2203/0405* (2013.01); *C01B 2203/042* (2013.01); *C01B 2203/06* (2013.01); *C12M 43/04* (2013.01)

(56) References Cited

U.S. PATENT DOCUMENTS

| | | |
|---|---|---|
| 8,444,725 B2 | 5/2013 | Agrawal |
| 9,617,566 B2 | 4/2017 | Collet |
| 9,834,792 B2 | 12/2017 | Trevethick |
| 10,119,196 B2 | 11/2018 | Sivasankar |
| 10,174,303 B2 | 1/2019 | Behrendorff |
| 10,358,662 B2 | 7/2019 | Simpson |
| 10,603,632 B2 | 3/2020 | Winter |
| 10,808,263 B2 | 10/2020 | Conrado |
| 11,053,517 B2 | 7/2021 | Conrado |
| 11,359,294 B2 | 6/2022 | Mihalcea |
| 2004/0265224 A1* | 12/2004 | Papavassiliou ......... C01B 3/382 422/628 |
| 2009/0031615 A1 | 2/2009 | Joshi |
| 2012/0156739 A1 | 6/2012 | Schultz |
| 2012/0252082 A1 | 10/2012 | Simpson |
| 2012/0309066 A1* | 12/2012 | Simpson ................ C01B 3/38 435/155 |
| 2013/0210096 A1 | 8/2013 | Schultz |
| 2013/0316424 A1 | 11/2013 | Simpson |
| 2014/0370559 A1 | 12/2014 | Oakley |
| 2015/0072387 A1 | 3/2015 | Collet |
| 2015/0247171 A1* | 9/2015 | Schultz .................. C12P 7/54 435/140 |
| 2016/0010116 A1 | 1/2016 | Collet |
| 2016/0115505 A1 | 4/2016 | Trevethick |
| 2016/0338380 A1 | 11/2016 | Simpson |
| 2016/0348087 A1 | 12/2016 | Behrendorff |
| 2017/0159083 A1 | 6/2017 | Valgepea |
| 2017/0175064 A1 | 6/2017 | Collet |
| 2017/0197829 A1 | 7/2017 | Andersen |
| 2017/0218404 A1 | 8/2017 | Simpson |
| 2019/0185887 A1 | 6/2019 | Foody |
| 2020/0087144 A1* | 3/2020 | Marker .................. C01B 3/40 |
| 2020/0354216 A1 | 11/2020 | Mortensen |
| 2020/0399664 A1 | 12/2020 | Conrado |
| 2022/0325216 A1 | 10/2022 | Conrado |
| 2022/0325217 A1 | 10/2022 | Conrado |
| 2022/0325218 A1 | 10/2022 | Conrado |
| 2022/0325227 A1 | 10/2022 | Conrado |
| 2022/0333140 A1 | 10/2022 | Conrado |

FOREIGN PATENT DOCUMENTS

| | | |
|---|---|---|
| WO | 2008115080 A1 | 9/2008 |
| WO | 2009151342 A1 | 12/2009 |
| WO | 2011112103 A1 | 9/2011 |
| WO | 2012015317 A1 | 2/2012 |
| WO | 2012026833 A1 | 3/2012 |
| WO | 2012053905 A1 | 4/2012 |
| WO | 2012024522 A3 | 5/2012 |
| WO | 2012054798 A3 | 8/2012 |
| WO | 2012115527 A3 | 1/2013 |
| WO | 2013036147 A3 | 8/2013 |
| WO | 2013180581 A1 | 12/2013 |
| WO | 2013180584 A1 | 12/2013 |
| WO | 2013185123 A1 | 12/2013 |
| WO | 2013191567 A1 | 12/2013 |
| WO | 2014036152 A1 | 3/2014 |
| WO | 2016094334 A1 | 6/2016 |
| WO | 2016152698 A1 | 9/2016 |
| WO | 2016191625 A1 | 12/2016 |
| WO | 2017066498 A1 | 4/2017 |

OTHER PUBLICATIONS

Ragsdale, nBiochim Biphys Acta, 1784: 1873-1898, 2008.
Written Opinion of the International Searching Authority for International Application No. PCT /US2018/049723, mailed Jan. 23, 2019 (p. 1-9).
Zhu, "Developments on CO2-utilization technologies" Clean Energy, 2019, vol. 3, No. 2, 85-100.

\* cited by examiner

PROCESS AND APPARATUS FOR PROVIDING A FEEDSTOCK

CROSS REFERENCE TO RELATED APPLICATION

This application claims the benefit of U.S. Provisional Patent Application No. 63/173,243, filed Apr. 9, 2021, the entirety of which is incorporated herein by reference.

FIELD

The disclosure relates to processes and apparatuses for providing a feedstock for producing one or more fermentation product. In particular, the disclosure relates to processes and apparatuses whereby a gaseous stream comprising at least one hydrocarbon is used to produce the feedstock for a gas fermentation unit.

BACKGROUND

Carbon dioxide ($CO_2$) accounts for about 76% of global greenhouse gas emissions from human activities, with methane (16%), nitrous oxide (6%), and fluorinated gases (2%) accounting for the balance (the United States Environmental Protection Agency). Reduction of greenhouse gas emissions, particularly $CO_2$, is critical to halting the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol.

Such gasses may be derived, for example, from industrial processes, including gas from carbohydrate fermentation, gas from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from steam sources including but not limited to steam methane reforming, steam naphtha reforming, petroleum coke gasification, catalyst regeneration, fluid catalyst cracking, catalyst regeneration-naphtha reforming, and dry methane reforming).

The substrate and/or C1-carbon source may be synthesis gas known as syngas, which may be obtained from reforming, partial oxidation, or gasification processes. Examples of reforming processes include, steam methane reforming, steam naphtha reforming, reforming of natural gas, reforming of biogas, reforming of landfill gas, naphtha reforming, and dry methane reforming. Examples of gasification processes include gasification of coal, gasification of refinery residues, gasification of petroleum coke, gasification of biomass, gasification of lignocellulosic material, gasification of waste wood, gasification of black liquor, gasification of municipal solid waste, gasification of municipal liquid waste, gasification of industrial solid waste, gasification of industrial liquid waste, gasification of refuse derived fuel, gasification of sewerage, gasification of sewerage sludge, gasification of sludge from wastewater treatment, gasification of biogas. Examples of partial oxidation processes include thermal and catalytic partial oxidation processes, catalytic partial oxidation of natural gas, partial oxidation of hydrocarbons.

With particular industrial or syngas processes, the composition of the gas may not be ideal for fermentation. When the composition of the gas is not ideal, cell growth, product selectivity, and stability may be less than optimal. Accordingly, there remains a need for a system and a process which provides an appropriate feedstock for a gas fermentation unit to promote product selectivity and stability in downstream fermentation process. For example, much of the demand for hydrogen in industry is met by methane steam reforming.

Conventionally, this reaction results in the production of CO and $H_2$ with little $CO_2$ as a by-product. The carbon monoxide is then reacted in one, or a series of two, water gas shift reactors to further generate $H_2$ and $CO_2$. Hydrogen is then purified in a pressure swing adsorption (PSA) unit. A purified hydrogen stream and a PSA tail gas comprising some hydrogen and unreacted $CO_2$ and CO are produced by the PSA unit. The PSA tail gas often has too little CO to be used directedly as a feed to gas fermentation. One technique to increase the CO concentration in the PSA tail gas involves utilizing only a high temperature water gas shift reactor. However, without an additional low temperature water gas shift reactor, the amount of purified hydrogen produced is less. Some refineries cannot suffer this loss of purified hydrogen in the purified hydrogen stream. A need exists for a process and system to maintain the high yield of purified hydrogen and yet provide a feed to gas fermentation having a suitable concentration of CO.

BRIEF SUMMARY

Disclosed is a process for providing a feedstock for a gas fermentation unit, wherein a first gaseous stream comprising $H_2$, CO, and $CO_2$ is passed to a hydrogen separation zone to produce a hydrogen enriched stream and a second gaseous stream comprising CO, $CO_2$ and $H_2$. The second gaseous stream is passed a $CO_2$ to CO conversion system to produce a third gaseous stream comprising $H_2$ and CO having a $H_2$:CO molar ratio of less than 5:1. The third gaseous stream is passed as the feedstock to the gas fermentation unit.

A gaseous feed stream comprising at least one hydrocarbon may be reformed in a reforming unit to produce a syngas stream comprising CO and $H_2$. The syngas stream may be passed to a water gas shift reaction zone for converting at least a portion of the CO into $CO_2$ and $H_2$ to provide the first gaseous stream. The water gas shift reaction zone may comprise at least one unit selected from a high temperature shift unit, a low temperature shift unit, and a combination thereof. The $CO_2$ to CO conversion system is at least one unit selected from reverse water gas reaction system, $CO_2$ electrolysis system, thermo-catalytic conversion system, electro-catalytic conversion system, partial combustion system or plasma conversion system. At least a portion of the CO or the $CO_2$ present in the second gaseous stream may be separated into a CO enriched gaseous stream or a $CO_2$ enriched gaseous stream prior to passing the second gaseous stream to the $CO_2$ to CO conversion system. The CO enriched gaseous stream may be passed to a location upstream or downstream of the $CO_2$ to CO conversion system and the $CO_2$ enriched gaseous stream may be recycled to the reforming unit. The third gaseous stream may be fermented in a gas fermentation unit to produce at least one fermentation product stream and an off-gas stream. The off-gas stream may be recycled to the reforming unit.

The disclosure further provides an apparatus for providing a feedstock. The apparatus comprises: a reforming unit in fluid communication with a gaseous feed line comprising at least one hydrocarbon; a water gas shift reaction zone in fluid communication with the reforming unit; a hydrogen separation zone in fluid communication with the water gas shift reaction zone and having a hydrogen stream outlet, and a second gaseous stream outlet; a $CO_2$ to CO conversion system in fluid communication with the second gaseous stream outlet; and a gas fermentation unit in fluid communication with the $CO_2$ to CO conversion system and having a product stream outlet and an off-gas stream outlet.

The water gas shift reaction zone may comprise at least one unit selected from a high temperature shift unit, a low temperature shift unit, and a combination thereof. The hydrogen separation zone is at least one unit selected from the group consisting of pressure swing adsorption unit, a membrane separation unit, and a combination thereof. The $CO_2$ to CO conversion system is at least one unit selected from reverse water gas reaction system, $CO_2$ electrolysis system, thermo-catalytic conversion system, electro-catalytic conversion system, partial combustion system and plasma conversion system.

In one embodiment, the apparatus further comprises an enrichment unit having a CO enriched stream outlet, and a $CO_2$ enriched gaseous stream outlet. The enrichment unit in fluid communication with the second gaseous stream outlet. The $CO_2$ to CO conversion system may be in fluid communication with the CO enriched gaseous stream outlet. The reforming unit may be further in fluid communication with the $CO_2$ enriched gaseous stream outlet, the off-gas stream outlet, or both. The gas fermentation unit is further in fluid communication with the hydrogen stream outlet.

DETAILED DESCRIPTION

Figure 1:
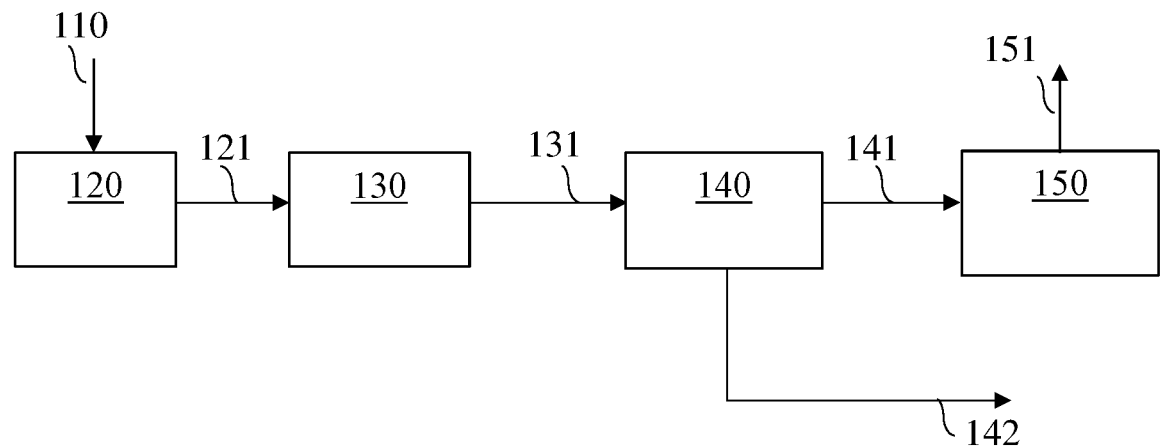
FIG. 1 is a schematic flow diagram depicting a process for providing a feedstock for a gas fermentation unit according to one embodiment.

The disclosure provides a process for generating a feedstock to a gas fermentation unit which improves the performance and/or the economics of the gas fermentation process. The disclosure has particular applicability to fermentation processes utilizing a gaseous feed stream initially lacking desired amounts of CO for fermentation. The process begins with a gaseous feed stream which may include any gas leaving an industrial process which comprises at least one hydrocarbon. In certain instances, the gaseous feed stream comprising at least one hydrocarbon may be a waste gas obtained as a by-product of an industrial process or from some other source. Examples include combustion engine exhaust fumes, biogas, landfill gas, fuel gas, naphtha. The hydrocarbon in the gaseous feed stream may methane.

In certain embodiments, the industrial process is selected from ferrous metal products manufacturing, such as a steel manufacturing, non-ferrous products manufacturing, petroleum refining, electric power production, carbon black production, paper and pulp manufacturing, ammonia production, methanol production, coke manufacturing, petrochemical production, carbohydrate fermentation, cement making, aerobic digestion, anaerobic digestion, catalytic processes, natural gas extraction, cellulosic fermentation, oil extraction, industrial processing of geological reservoirs, processing fossil resources such as natural gas coal and oil, landfill operations, or any combination thereof. Examples of specific processing steps within an industrial process include catalyst regeneration, fluid catalyst cracking, and catalyst regeneration. Specific examples in steel and ferroalloy manufacturing include blast furnace gas, basic oxygen furnace gas, coke oven gas, direct reduction of iron furnace top-gas, and residual gas from smelting iron. Other general examples include flue gas from fired boilers and fired heaters, such as natural gas, oil, or coal fired boilers or heaters, and gas turbine exhaust. In these embodiments, the hydrocarbon may be captured from the industrial process before it is emitted into the atmosphere, using any known method.

The hydrocarbon in the gaseous feed stream may be a gas stream comprising methane. Such a methane containing gas may be obtained from: fossil methane emissions such as during fracking, wastewater treatment, livestock, agriculture, and municipal solid waste landfills.

In an embodiment, the process comprises steam reforming, auto-thermal reforming, dry reforming or conducting partial oxidation of the at least one hydrocarbon present of the gaseous feed stream to produce a syngas stream comprising at least CO and $H_2$ and $CO_2$ that was present in the gaseous feed stream. For ease of understanding the disclosure is presented in terms of steam reforming, but the scope is not limited to steam reforming. Techniques such as auto-thermal reforming, dry reforming or partial oxidation may be employed.

The syngas stream produced is passed to a water gas shift reaction zone, wherein at least a portion of the CO in the syngas stream is converted into $CO_2$ and $H_2$ providing a first gaseous stream. The water gas shift reaction zone comprises at least one unit selected from a high temperature shift unit, a low temperature shift unit, or a combination thereof.

In many industrial processes, hydrogen is a valuable resource. Wherever possible it is desirable to separate hydrogen if not needed for a given process and redirect the hydrogen to another process where it is needed. Therefore, the first gaseous stream comprising $H_2$, CO, and $CO_2$ produced from the gaseous feed stream is treated to remove at least a portion of hydrogen. The first gaseous stream is passed to a hydrogen separation zone to produce a hydrogen enriched stream and a second gaseous stream comprising CO, $CO_2$ and reduced $H_2$. The hydrogen enriched stream comprising the separated hydrogen is generated primarily for use elsewhere, but a portion may be supplied directly to the bioreactor.

The hydrogen separation zone may be at least one unit selected from a pressure swing adsorption unit (PSA), a membrane separation unit, or a combination thereof. Pressure swing adsorption processes provide an effective technique to remove at least a portion of the hydrogen from a gaseous stream. When the first gaseous stream from the water gas shift system is passed through a pressure swing adsorption process and hydrogen is removed and a $CO_2$ and CO enriched PSA tail gas stream at a low pressure is generated. Membrane separation modules provide a low cost, simple way to remove at least a portion of hydrogen from a gaseous stream. When the first gaseous stream from the water gas shift system is passed through a membrane separation module, a high-pressure $CO_2$ and CO enriched stream and a low-pressure $H_2$ enriched stream are generated.

At this point, a hydrogen stream has been generated to meet hydrogen demands elsewhere. The $CO_2$ and CO enriched stream from the hydrogen separation unit is targeted for use as a feed to a gas fermentation unit. However, traditionally, the $CO_2$ and CO enriched stream from the hydrogen separation unit contains too little CO for direct use as a feed to gas fermentation and modification are necessary to provide the correct ratios of components in a feed to gas fermentation.

Embodiments may be described by reference to the process configurations shown in FIGS. 1 to 5, which relate to both apparatus and methods to carry out the disclosure. Any reference to a method "step" includes reference to an apparatus "unit" or equipment that is suitable to carry out the step, and vice-versa.

FIG. 1 shows a schematic flow diagram of one embodiment. At least a portion of gaseous feed stream 110 comprising at least one hydrocarbon is passed to steam reforming unit 120 where the hydrocarbon in gaseous feed stream is steam reformed to produce syngas stream 121 comprising at least CO and $H_2$. At least a portion of syngas stream 121 may be passed to water gas shift reaction zone 130 where a portion of the CO is shifted to $CO_2$ and $H_2$ to provide first gaseous stream 131. First gaseous stream 131 is passed to hydrogen separation zone 140 where at least a portion of hydrogen is separated from first gaseous stream 131 to form hydrogen enriched stream 142 and second gaseous stream comprising at least CO, $CO_2$, and the remaining $H_2$. Second gaseous stream 141 is passed to gas fermentation unit 150 as a feedstock to produce at least one fermentation product which is removed from gas fermentation unit 150 as product stream 151. In this embodiment, in order for second gaseous stream 141 to have sufficient CO for gas fermentation, water gas shift reaction zone 130 comprises (i) only a high temperature water gas shift reactor, or comprises (ii) both a high temperature water gas shift reactor and a low temperature water gas shift reactor, but when both a high temperature- and a low temperature-water gas shift reactor are present, at least a portion of the effluent of the high temperature water gas shift reactor is bypassed around the low temperature water gas shift reactor. In this way, the amount of CO present in the second gaseous stream 141 remains sufficient for gas fermentation. However, the consequence is a loss in the quantity of hydrogen in the hydrogen enriched stream that is produced.

In one embodiment, hydrogen separation zone 140 may comprise at least one membrane separation module. In another embodiment, the hydrogen separation zone 140 may comprise at least one pressure swing adsorption system. In yet another embodiment hydrogen separation zone 140 may comprise at least one membrane separation module and at least one pressure swing adsorption system.

In certain embodiments, gaseous feed stream 110 comprising at least one hydrocarbon is derived at least in part from an industrial source. As discussed above, the industrial source may be selected from carbohydrate fermentation, gas fermentation, cement making, pulp and paper making, steel making, oil refining and associated processes, petrochemical production, coke production, anaerobic or aerobic digestion, synthesis gas, natural gas extraction, oil extraction, metallurgical processes, for production and/or refinement of aluminium, copper, and/or ferroalloys, geological reservoirs, and catalytic processes.

The gas fermentation unit comprises at least one bioreactor system which includes a fermentation device consisting of one or more vessels and/or towers or piping arrangements. Suitable examples include, continuous stirred tank reactor, immobilized cell reactor, trickle bed reactor, bubble column, gas lift fermentor, static mixer, circulated loop reactor, membrane reactor, such as a hollow fiber membrane bioreactor, or other vessel or other device suitable for gas-liquid contact. The bioreactor may be adapted to receive a gaseous substrate comprising CO and $H_2$, or CO, $CO_2$ and $H_2$. The bioreactor may comprise multiple reactors, either in parallel or in series. The bioreactor may be configured to receive an inoculum from an invocation reactor. The bioreactor may be configured as a production reactor, where most of the fermentation products are produced.

In one embodiment, fermentation product produced in the gas fermentation unit 150 may be selected from ethanol, acetate, butanol, butyrate, 2,3-butanediol, 1,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, 1-propanol, monoethylene glycol, isobutene, and C6-C14 alcohols. In various instances, at least a portion of the fermentation product may be further converted to at least one component of diesel fuel, jet fuel, gasoline, propylene, nylon 6-6, rubber, and/or resins. In some embodiments, at least one fermentation product may be a microbial biomass. This microbial biomass may be further processed to produce at least one component of animal feed.

In an alternative embodiment, to maximize the amount of hydrogen produced in the hydrogen enriched stream, the process further comprises passing the second gaseous stream to a $CO_2$ to CO conversion system to produce a third gaseous stream enriched in CO. The $CO_2$ to CO conversion system, such as a reverse water gas shift unit, reacts some of the $H_2$ and $CO_2$ in the second gaseous stream to generate the needed CO ($H_2+CO_2 \rightarrow CO+H_2O$) in order to support the performance and/or the economics of a fermentation process. It is advantageous to shift some amount of $H_2$ to CO to aid in fermentation especially in situations where otherwise the second gaseous stream would contain very low concentrations of CO. This situation may arise, for example, in some refineries where the CO content of the waste gas stream, such as the PSA tail gas, is very low, and perhaps less than ideal for the gas fermentation process. The reaction of $CO_2$ in the $CO_2$ to CO conversion system is targeted to produce a third gaseous stream having a $H_2$:CO molar ratio less than 5:1; or less than 4:1, or less than 3:1.

The $CO_2$ to CO conversion system is at least one unit selected from reverse water gas reaction system, $CO_2$ electrolysis system, thermo-catalytic conversion system, electro-catalytic conversion system, partial combustion system or plasma conversion system. The reverse water gas reaction unit (rWGR) produces water from carbon dioxide and hydrogen, with carbon monoxide as a side product. The reverse water gas reaction unit may comprise a single stage or more than one stage. The different stages may be conducted at different temperatures and may use different catalysts. The thermo-catalytic conversion disrupts the stable atomic and molecular bonds of $CO_2$ and other reactants over a catalyst by using thermal energy as the driving force of the reaction to produce CO. Since $CO_2$ molecules are thermodynamically and chemically stable, if $CO_2$ is used as a single reactant, large amounts of energy are required. Therefore, often other substances such as hydrogen are used as a co-reactant to make the thermodynamic process easier. Many catalysts are known for the process such as metals and metal oxides as well as nano-sized catalyst metal-organic frameworks. Various carbon materials have been employed as carriers for the catalysts. The electro-catalytic conversion is the electrocatalytic reduction of carbon dioxide to produce synthesis gas from water and carbon dioxide. Such electro-catalytic conversion, also referred to as electrochemical conversion, of carbon dioxide typically involves electrodes in an electrochemical cell having a solution supporting an electrolyte through which carbon dioxide is bubbled, see for example U.S. Pat. No. 10,119,196. The synthesis gas, also known as syngas, produced comprises CO, and is separated from the solution of the electrochemical cell and removed. The combination of photocatalysis and electrocatalysis in photoelectrocatalysis which uses for example sunlight irradiation is also a suitable variation.

Figure 2:
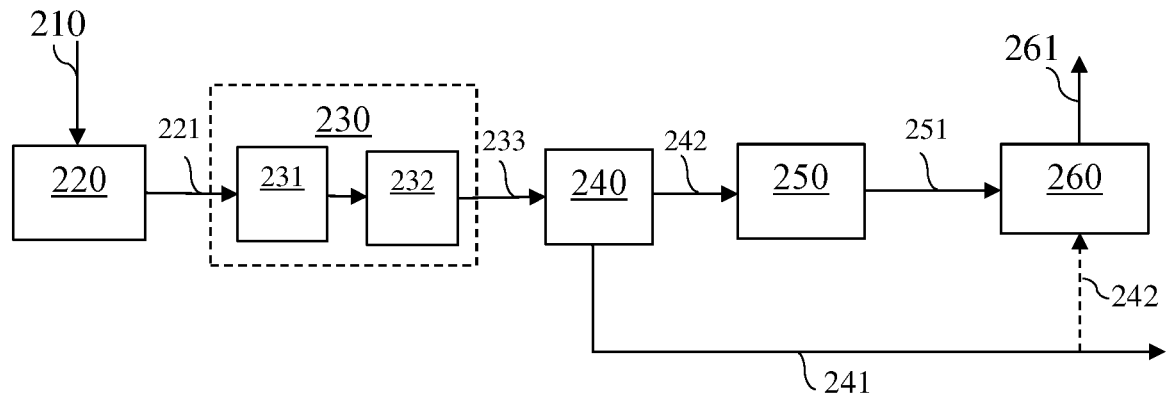
FIG. 2 is a schematic flow diagram depicting the integration of process for providing a feedstock to a gas fermentation unit, with a $CO_2$ to CO conversion system upstream of the gas fermentation unit, in accordance with one embodiment.

FIG. 2 shows a schematic flow diagram of one embodiment. At least a portion of gaseous feed stream 210 is passed to reforming unit 220 to produce a syngas stream 221 comprising at least CO and $H_2$. At least a portion of syngas stream is passed to water gas shift reaction zone 230 to generate first gaseous stream. In the embodiment illustrated, water gas shift reaction zone comprises the combination of high temperature shift unit 231 and low temperature shift unit 232. The First gaseous stream 233 may be passed to hydrogen separation zone 240. At least a portion of the hydrogen may be separated from the first gaseous stream into a hydrogen enriched stream 241 and second gaseous stream 242 comprising CO, $CO_2$ and $H_2$. Second gaseous stream is passed to $CO_2$ to CC) conversion system 250 to produce third gaseous stream comprising at least $H_2$ and CO. The $H_2$:CO molar ratio in the third gaseous stream may be less than 5:1. Third gaseous stream 251 is passed to gas fermentation unit, 260 as a feedstock to produce fermentation product stream 261. At least a portion of the hydrogen enriched stream 241, separated from the first gaseous stream, may be passed to the gas fermentation unit 260.

In an embodiment the $H_2$:CO molar ratio in the third gaseous stream may be less than 4:1. In certain embodiments $H_2$:CO molar ratio in the third gaseous stream may be less than 3:1.

In some embodiments, hydrogen separation zone 240 comprises at least one membrane separation module or at least one pressure swing adsorption process. In another embodiment, the hydrogen separation zone 240 removes at least a portion of hydrogen through use of both a membrane separation module and a pressure swing adsorption process.

In various embodiments, $CO_2$ to CO conversion system 250 is at least one unit selected from reverse water gas reaction system, $CO_2$ electrolysis system, thermo-catalytic conversion system, electro-catalytic conversion system, partial combustion system, or plasma conversion system.

In certain instances, gaseous feed stream 210 passed to the reforming unit 220 may be derived at least in part from an industrial source. The industrial source may be selected from carbohydrate fermentation, gas fermentation, cement making, pulp and paper making, steel making, oil refining and associated processes, petrochemical production, coke production, anaerobic or aerobic digestion, synthesis gas, natural gas extraction, oil extraction, metallurgical processes, for production and/or refinement of aluminium, copper, and/or ferroalloys, geological reservoirs, and catalytic processes.

Fermentation product in product stream 261 produced in the gas fermentation unit 260 may be ethanol, acetate, butanol, butyrate, 2,3-butanediol, 1,3-butanediol, lactate, butene, butadiene, methyl ethyl ketone, ethylene, acetone, isopropanol, lipids, 3-hydroxypropionate, isoprene, fatty acids, 2-butanol, 1,2-propanediol, 1-propanol, monoethylene glycol, isobutene, and C6-C14 alcohols. In various instances, at least a portion of the fermentation product may be further converted to at least one component of diesel fuel, jet fuel, gasoline, propylene, nylon 6-6, rubber, and/or resins. In various embodiments, at least one fermentation product may be a microbial biomass. This microbial biomass may be further processed to produce at least one component of animal feed.

In a specific embodiment of FIG. 2, gaseous feed stream 210 comprises a methane containing gaseous feed, reforming unit 220 comprises a methane steam reformer, hydrogen separation zone 240 comprises a pressure swing adsorption unit, and second gaseous stream 242 comprises a pressure swing adsorption unit tail gas.

Figure 3:
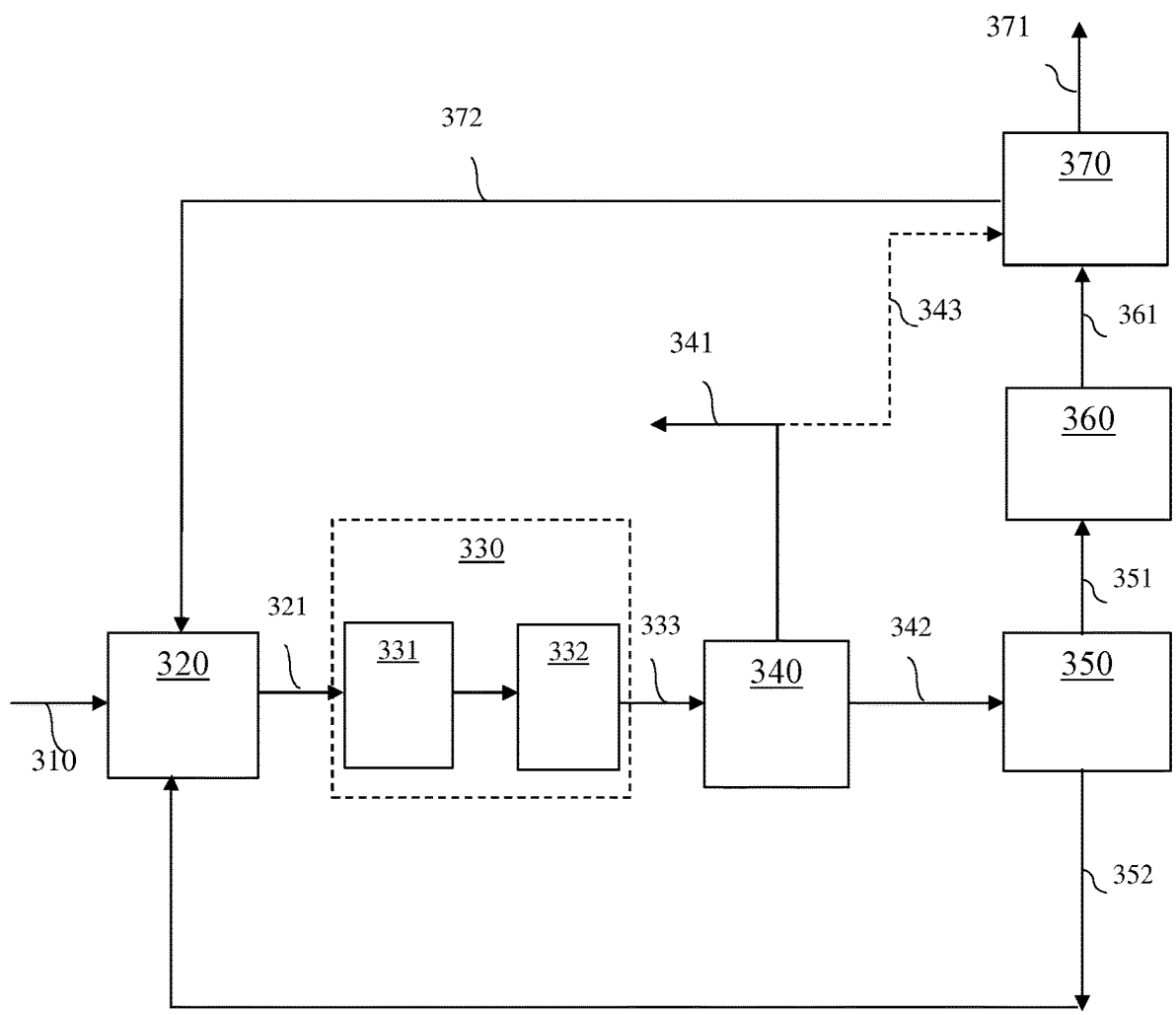
FIG. 3 is a schematic flow diagram depicting the integration of process for providing a feedstock with at least one separation unit and a $CO_2$ to CO conversion system upstream of the gas fermentation unit, in accordance with one embodiment.

FIG. 3 shows one embodiment utilizing a first gaseous stream from a reforming process. At least a portion of gaseous feed stream 310 comprising at least one hydrocarbon is flowed to reforming unit 320 to produce syngas stream 321 comprising at least CO and $H_2$. At least a portion of syngas stream 321 is passed to water gas shift reaction zone 330 to convert at least a portion of the CO into $CO_2$ and $H_2$ and provide first gaseous stream 333. The water gas shift reaction zone 330 comprises high temperature shift unit 331 and low temperature shift unit 332. First gaseous stream 333 is passed to hydrogen separation zone 340.

In various embodiments, the process may comprise multiple separation processes 340, 350. As shown in FIG. 3, the first gaseous stream 333 is passed to hydrogen separation zone 340 to separate at least a portion of the hydrogen into hydrogen enriched stream 341 and a second gaseous stream 342 comprising CO, $CO_2$ and $H_2$. Second gaseous stream 342 is passed to enrichment unit 350. At least a portion of the CO or the $CO_2$ present in second gaseous stream is separated into a CO enriched gaseous stream 351 or a $CO_2$ enriched gaseous stream 352. The CO enriched gaseous stream 351 is passed to $CO_2$ to CO conversion system 360 to produce third gaseous stream 361 comprising at least $H_2$ and CO. The $H_2$:CO molar ratio in third gaseous stream may be less than 5:1. Third gaseous stream 361 may be fed to gas fermentation unit 370 to produce at least one fermentation product stream 371 and off-gas stream 372. At least a portion of hydrogen enriched stream 343, separated from the first gaseous stream 333, may be passed to gas fermentation unit 370. Off-gas stream 372 is recycled to reforming unit 320. $CO_2$ enriched gaseous stream 352 is recycled to reforming unit 320.

In an embodiment the $H_2$:CO molar ratio in the third gaseous stream may be less than 4:1. In certain embodiments $H_2$:CO molar ratio in the third gaseous stream may be less than 3:1.

In various embodiments, gas fermentation unit 370 comprises one or more inoculation reactors and one or more bioreactors configured in a stepwise manner, whereby the inoculation reactor(s) ferments a CO enriched gaseous stream to produce an inoculum, which is then fed to the bioreactor(s). By utilizing this inoculum in the bioreactor, product selectivity and stability of the fermentation process is improved.

The term "gas fermentation unit" may further comprise an "inoculation reactor", "inoculator", "seed reactor" and the like which includes a fermentation device for establishing and promoting cell growth. The inoculation reactor may be adapted to receive a gaseous substrate comprising CO or $CO_2$ or $H_2$ or mixtures thereof. The inoculation reactor is a reactor where cell growth is first initiated. In various embodiments, the inoculation reactor is where previously growth cells are revived. In the various embodiments, the inoculator initiates cell growth of one or more microorganism to produce an inoculum, which may then be transferred to the bioreactor system where each bioreactor is configured to promote the production of one or more fermentation product. In certain instances, the inoculator has a reduced volume when compared to the subsequent one or more bioreactor.

The term "inoculum" is intended to encompass the fermentation broth initially grown in the inoculation reactor which is then passed to the one or more subsequent bioreactors to seed the one or more subsequent bioreactor. The inoculum is utilized by the one or more bioreactors to produce one or more fermentation product.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

Figure 4:
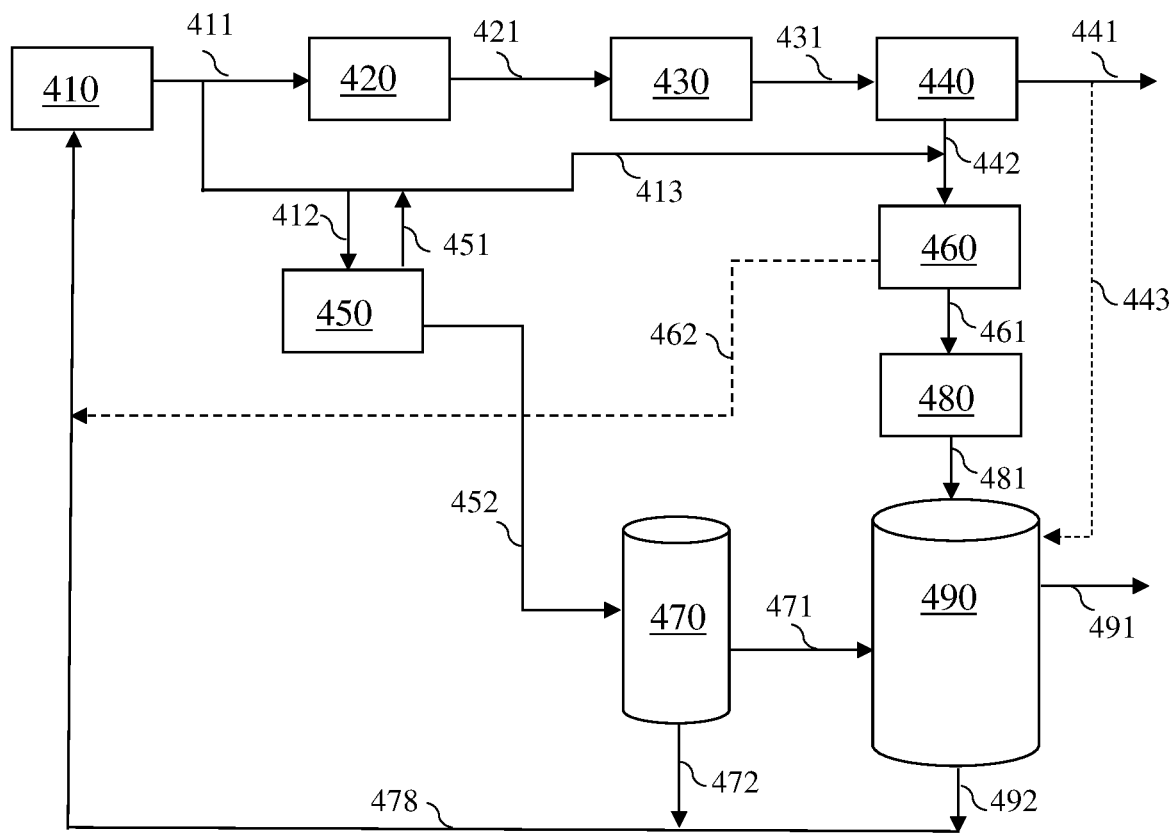
FIG. 4 is a schematic flow diagram depicting the integration of process for providing a feedstock with at least one water-gas-shift reaction zone, at least one hydrogen separation unit, and a $CO_2$ to CO conversion system, upstream of the gas fermentation unit, in accordance with one embodiment.
Figure 5:
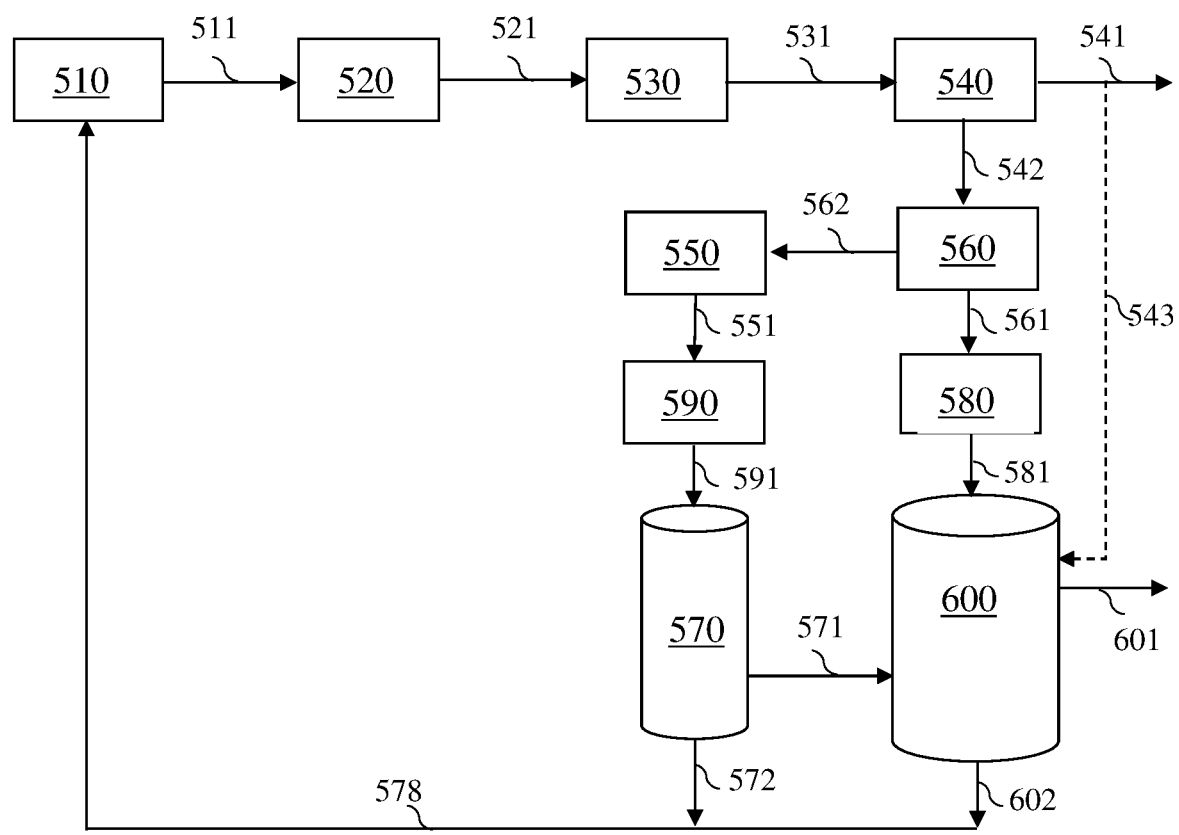
FIG. 5 is a schematic flow diagram further depicting the integration of process for providing a feedstock, with a $CO_2$ to CO conversion system and two hydrogen separation units upstream of the fermentation unit, in accordance with one embodiment.

FIGS. 4 and 5 depict various embodiments using a hydrogen production process of a refining operation as the industrial source of the gaseous feed stream comprising at least one hydrocarbon. A typical hydrogen production process, as depicted in FIG. 4 and FIG. 5, contains the following stages: (i) a reforming process wherein a $CH_4$ containing feedstock is converted to a syngas stream comprising CO and $H_2$; (ii) at least one water gas shift reaction zone, wherein a portion of the CO is reacted with water to produce first gaseous stream comprising $H_2$ and $CO_2$; (iii) a hydrogen separation zone adapted to recover hydrogen enriched stream from the first gaseous stream; and (iv) a $CO_2$ to CO conversion system to produce a third gaseous stream comprising $H_2$ and CO and having $H_2$:CO molar ratio less than 5:1.

As shown in FIG. 4, the C1-containing gaseous substrate may first be passed to a reforming unit 410 to convert at least a portion of the $CH_4$ to a syngas stream 411 comprising CO and $H_2$. Syngas stream 411 is passed to water gas shift zone 420 to shift at least a portion of the CO into $CO_2$ and $H_2$ to provide first gaseous stream 421. First gaseous stream 421 is passed to one or more further water gas shift reaction zone 430 and be fed to the one or more hydrogen removal process 440 via piping means 431 to separate first gaseous stream 421 into hydrogen enriched stream 441 and mixed gaseous stream 442 comprising CO, $CO_2$ and $H_2$. Mixed gaseous stream 442 is passed to one or more further hydrogen separation zone 460 to generate second gaseous stream 461. Second gaseous stream 461 from the one or more further hydrogen separation zone 460 is passed to $CO_2$ to CO conversion system 480 to produce a third gaseous stream 481 comprising $H_2$ and CO. $H_2$:CO molar ratio in the third gaseous stream may be less than 5:1. Third gaseous stream 481 is passed as a feedstock, to gas fermentation unit 490 for fermentation. At least a portion of second gaseous stream 462 may optionally be passed to reforming process 410. Optionally, at least a portion of hydrogen enriched stream 443 may be passed to the gas fermentation unit 490. In various instances, gas fermentation unit 490 receives third gaseous substrate 481 and produces one or more fermentation products in fermentation product stream 491.

In another embodiment, as shown in FIG. 4, a C1-containing stream 413 from a reforming process 410 may be mixed with the mixed gaseous stream 442 and passed to one or more further hydrogen separation zone 460. A C1-containing stream 412 is flowed to pressure swing adsorption process 450 provided upstream of the inoculation reactor 470. The pressure swing adsorption process 450 separates the C1-containing stream into a high-pressure $H_2$ rich stream and a low-pressure CO-rich stream. The low-pressure CO-rich stream may be passed to a compressor prior to being passed to the inoculation reactor 470 via piping means 452. The separated hydrogen stream 451 may be passed from the pressure swing adsorption process 450 to another pressure swing adsorption process 460. Optionally, inoculator off-gas stream 472 from both inoculation reactor 470 and gas fermentation off gas stream 492 from gas fermentation unit 490 may be passed back to reforming process 410 independently and or in combined stream 478.

In an embodiment the $H_2$:CO molar ratio in the third gaseous stream may be less than 4:1. In certain embodiments $H_2$:CO molar ratio in the third gaseous stream may be less than 3:1.

In the various embodiments, the inoculation reactor 470 and the gas fermentation unit 490 are configured in a stepwise manner, whereby the inoculation reactor 470 ferments a CO-rich C1-containing gaseous substrate to produce an inoculum 471, which is then fed to the gas fermentation unit 490. By utilizing inoculum 471 in gas fermentation unit 490, product selectivity and stability of the fermentation process is improved.

In another embodiment, as shown in FIG. 5, the C1-containing stream from the reforming unit 510 may be passed to multiple hydrogen separation zones 540, 550, 560, 590 before being passed to either the inoculation reactor 570 and/or the gas fermentation unit 600. In various instances, the C1-containing stream may be passed through a compressor before and/or between a hydrogen removal process. By passing the C1-containing stream to multiple hydrogen separation zones the CO composition in the C1-containing stream may be further enriched.

In various embodiments, the process may include multiple water gas shift reaction zones 520, 530 in combination with multiple hydrogen separation zones 540, 550, 560. As shown in FIG. 5, the C1-containing gaseous substrate may first be passed from a reforming unit 510 to convert at least a portion of the $CH_4$ to a syngas stream 511 comprising CO and $H_2$. Syngas stream 511 is passed to a water gas shift reaction zone 520 to shift at least a portion of the CO into $CO_2$ and $H_2$ to provide first gaseous stream 521. First gaseous gas stream 521 is passed to one or more further water gas shift reaction zone 530 and the effluent 531 passed one or more hydrogen separation zone 540 to separate first gaseous stream 521 into hydrogen enriched stream 541 and mixed gaseous stream 542 comprising CO, $CO_2$ and $H_2$. Mixed gaseous stream 542 is passed to one or more further hydrogen separation zone 560 to generate second gaseous stream 561. Second gaseous stream 561 from the one or more further hydrogen separation zone 560 may be sent to $CO_2$ to CO conversion system 580 to produce a third gaseous stream 581 comprising $H_2$ and CO. $H_2$:CO molar ratio in the third gaseous stream may be less than 5:1. The third gaseous stream 581 is passed as a feedstock, to gas fermentation unit 600 for fermentation. At least a portion of second gaseous stream 562 not passed to the gas fermentation unit may optionally be passed to a subsequent hydrogen separation zone 550 and optionally in stream 551 to a further hydrogen separation zone 590, which ultimately may be passed as stream 591 to inoculation reactor 570, to produce an inoculum.

In an embodiment the $H_2$:CO molar ratio in the third gaseous stream may be less than 4:1. In certain embodiments $H_7$:CO molar ratio in the third gaseous stream may be less than 3:1.

In various instances, gas fermentation unit 600 receives gaseous substrate 581 and produces one or more fermentation products in product stream 601. Optionally, inoculator off-gas stream 572 and gas fermentation off gas stream 602 may be passed back to reforming unit 510 independently or combined into combined off gas stream 578. Optionally, at least a portion of the hydrogen enriched stream 543 may be passed to gas fermentation unit 600.

In various embodiments, inoculation reactor 570 and gas fermentation unit 600 are configured in a stepwise manner, whereby inoculation reactor 570 ferments a CO-rich C1-containing gaseous substrate to produce an inoculum 571, which is then fed to gas fermentation unit 600. By utilizing this inoculum in gas fermentation unit 600, product selectivity and stability of the fermentation process is improved.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the disclosure (especially in the context of the following claims) are to be construed to cover both the singular and the plural unless otherwise indicated herein or clearly contradicted by context. The terms "comprising," "having," "including," and "containing" are to be construed as open-ended terms (i.e., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means ±20% of the indicated range, value, or structure, unless otherwise indicated.

The recitation of ranges of values herein is merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Multiple embodiments are described herein. Variations of those embodiments may become apparent to those of ordinary skill in the art upon reading the foregoing description. Skilled artisans may employ such variations as appropriate, and it is intended for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A process for providing a feedstock, comprising:
   a) providing a stream comprising methane to a methane reforming process to produce a first gaseous stream comprising $H_2$, CO, and $CO_2$;
   b) passing the first gaseous stream to a water gas shift (WGS) process to produce a second gaseous stream comprising a reduced amount of CO and an increased amount of $H_2$ and $CO_2$;
   c) passing the first second gaseous stream to a hydrogen separation zone to produce a hydrogen enriched stream and a third gaseous stream comprising CO, $CO_2$ and a reduced amount of $H_2$;
   d) passing the third gaseous stream to a reverse water gas shift process to produce a fourth gaseous stream having an increased amount of CO such that the $H_2$ and CO are present in the fourth gaseous stream at a $H_2$:CO molar ratio of 4:1 or less; and
   e) passing the third fourth gaseous stream to a gas fermentation unit.

2. The process of claim 1 wherein the hydrogen separation zone comprises at least one unit selected from a pressure swing adsorption unit, a membrane separation unit, or a combination thereof.

3. The process of claim 1 further comprising separating at least a portion of the CO or the $CO_2$ present in the third gaseous stream into a CO enriched gaseous stream or a $CO_2$ enriched gaseous stream prior to passing the third gaseous stream to the reverse water gas shift process.

4. The process of claim 3 further comprising passing the CO enriched gaseous stream to a location upstream of the reverse water shift process.

5. The process of claim 1, further comprising separating at least a portion of the $CO_2$ present in the third gaseous stream into a $CO_2$ enriched gaseous stream and passing the $CO_2$ enriched gaseous stream to the methane reforming process.

6. The process of claim 1 further comprising fermenting the fourth gaseous stream in the gas fermentation unit to produce at least one fermentation product and an off-gas stream.

7. The process of claim 6, further comprising recycling the off-gas stream to the methane reforming process.

8. A process for providing a feedstock, comprising:
a) providing a stream comprising methane to a methane reforming process to produce a first gaseous stream comprising $H_2$, CO, and $CO_2$;
b) passing the first gaseous stream to a water gas shift (WGS) process to produce a second gaseous stream comprising a reduced amount of CO and an increased amount of $H_2$ and $CO_2$;
c) passing the second gaseous stream to a hydrogen separation zone to produce a hydrogen enriched stream and a third gaseous stream comprising CO, $CO_2$ and a reduced amount of $H_2$;
d) separating at least a portion of the CO or $CO_2$ in the third gaseous stream into a CO enriched gaseous stream or a $CO_2$ enriched gaseous stream prior to passing the third gaseous stream to a reverse water gas shift process to convert $CO_2$ to CO;
e) producing a fourth gaseous stream using the reverse water gas shift process, the fourth gaseous stream having an increased amount of CO such that the $H_2$ and CO are present in the fourth stream at a $H_2$:CO molar ratio of less than 4:1; and
f) passing the fourth gaseous stream to a gas fermentation unit.

9. The process of claim 8, wherein the CO enriched gaseous stream is passed to a location upstream of the reverse water shift process.

10. The process of claim 8, wherein the $CO_2$ enriched stream of step (d) is passed to the methane reforming process.

11. The process of claim 8 wherein the hydrogen separation zone comprises at least one unit selected from a pressure swing adsorption unit, a membrane separation unit, or a combination thereof.

12. The process of claim 8 further comprising fermenting the fourth gaseous stream in the gas fermentation unit to produce at least one fermentation product and an off-gas stream.

13. The process of claim 12, further comprising recycling the off-gas stream to the methane reforming process.

* * * * *